(12) United States Patent
Morton et al.

(10) Patent No.: US 8,321,242 B1
(45) Date of Patent: Nov. 27, 2012

(54) PERSONALIZED TIME RELEASE MESSAGING

(75) Inventors: Robert Charles Morton, Louisville, KY (US); Paul Joseph Mastracchio, San Clemente, CA (US); Craig Cooke, Ladera Ranch, CA (US)

(73) Assignee: Fox Chase Bank, Hatboro, PA (US)

( * ) Notice: Subject to any disclaimer, the term of this patent is extended or adjusted under 35 U.S.C. 154(b) by 255 days.

(21) Appl. No.: 12/592,307

(22) Filed: Nov. 23, 2009

Related U.S. Application Data

(60) Provisional application No. 61/122,611, filed on Dec. 15, 2008, provisional application No. 61/119,183, filed on Dec. 2, 2008.

(51) Int. Cl.
*G06Q 50/00* (2012.01)

(52) U.S. Cl. .............................................. 705/3; 705/2

(58) Field of Classification Search ................. 705/2–3
See application file for complete search history.

(56) References Cited

U.S. PATENT DOCUMENTS

| | | | |
|---|---|---|---|
| 6,305,377 B1 * | 10/2001 | Portwood et al. | 128/897 |
| 6,578,003 B1 * | 6/2003 | Camarda et al. | 705/3 |
| 6,988,075 B1 * | 1/2006 | Hacker | 705/3 |
| 2007/0168228 A1 * | 7/2007 | Lawless | 705/2 |
| 2007/0174092 A1 * | 7/2007 | Lara et al. | 705/3 |
| 2007/0299694 A1 * | 12/2007 | Merck | 705/3 |

* cited by examiner

*Primary Examiner* — Sind Phongsvirajati
(74) *Attorney, Agent, or Firm* — Frost Brown Todd LLC

(57) ABSTRACT

Media devices containing instructions which can allow patients to enroll and participate in time release messaging programs can be provided to patients by doctors who record personalized messages which are played when the devices are used. These media devices (or instructions from those devices stored on a user computer) can communicate with external systems to receive updates, both in terms of content and timing of information.

12 Claims, 14 Drawing Sheets

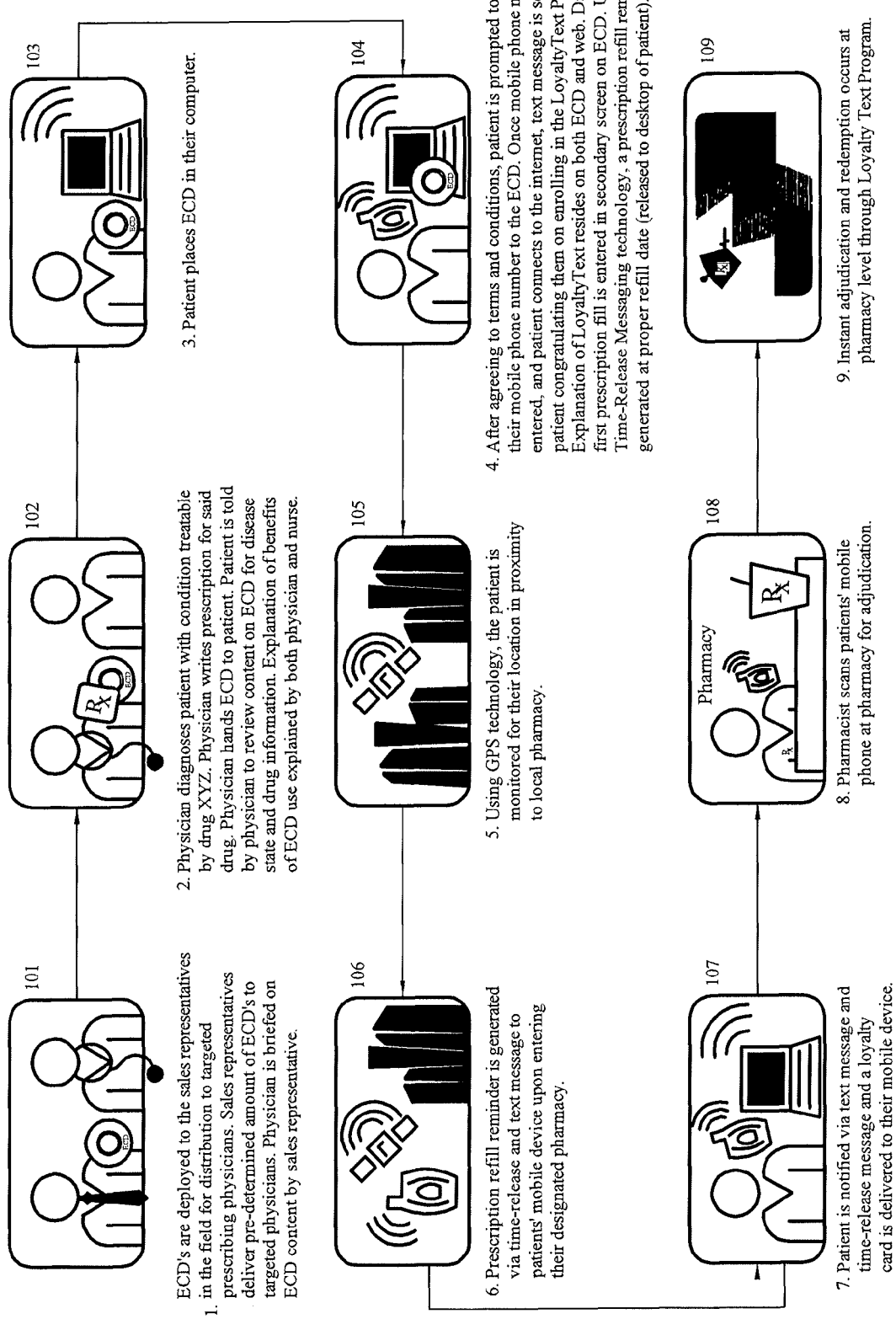

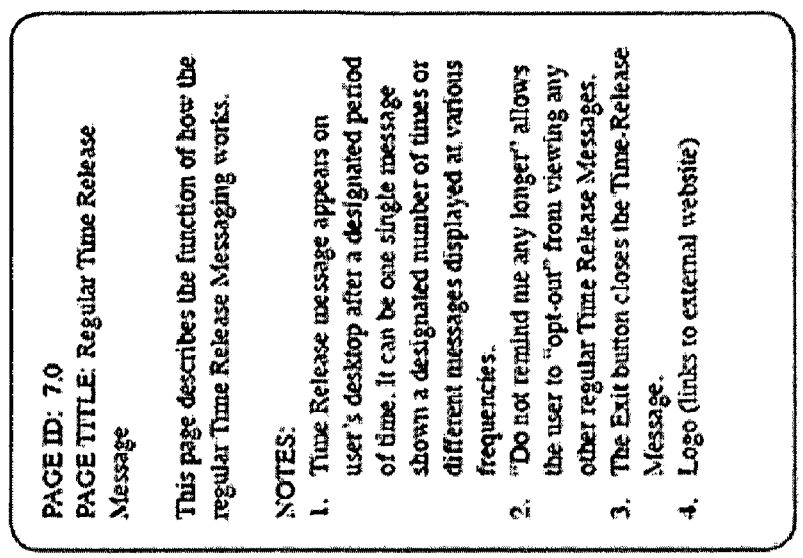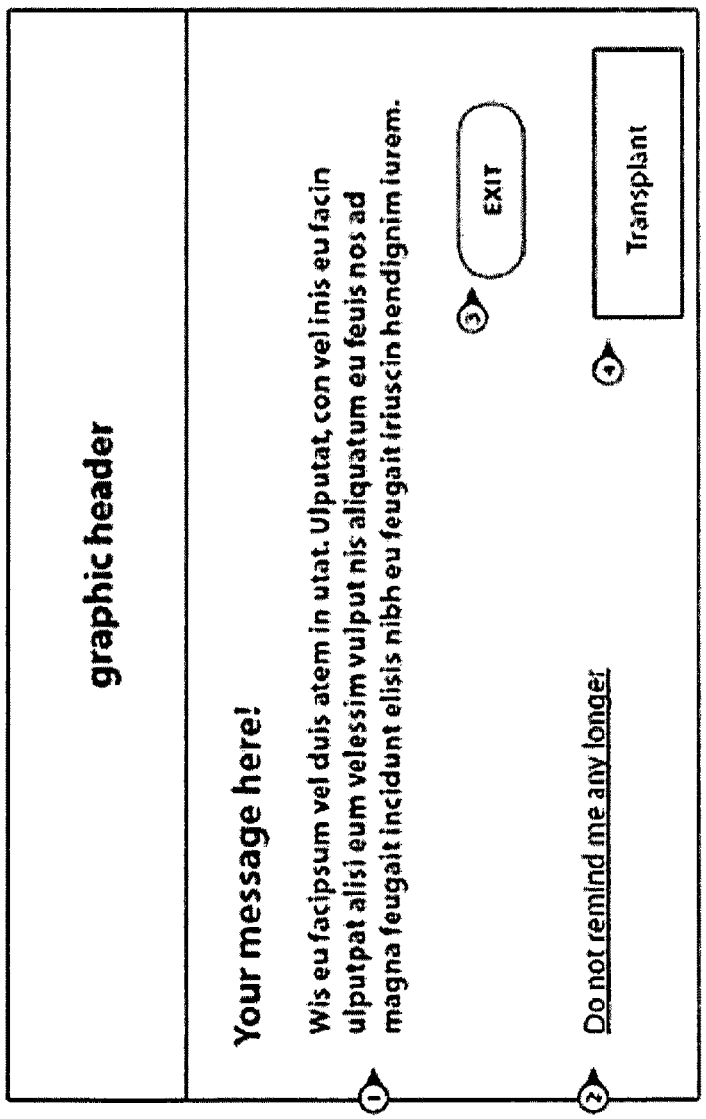
Figure 2c

PAGE ID: 4.1
PAGE TITLE: Medication Reminder Setup

This page allows the user to setup and start receiving text messages on a mobile device.

NOTES:
1. Text entry boxes for entering phone number.
2. Drop down menu with a list of time zones (Eastern, Central, and Pacific only). It's probably safest to use Pacific as the default since a later message won't wake somebody up in the middle of the night.
3. Drop down menu of times broken down into 30 minute increments (6:00 am, 6:30am, 7:00am, etc). The list of times will be limited to the morning hours starting at 3:00am and ending with 11:30am.
4. Check box must be selected in order for the submission to go through.
5. Clicking on the T&C link opens the T&C pop-up window.
6. Submit button activates the transfer of data to Sumo/Text. An "Almost Done" message is displayed on the computer once the data has been transferred successfully and an opt-in text message is sent to the mobile device.

TRANSPLANT EXPERIENCE LOGO

Home
Transplant Experience
Medication Reminder
Prescription Refill Reminder
Educational Resources
- Transplant Experience News
- Sharing Life
- Prograf and You
- Cholesterol and Your New Organ
- Blood Pressure and Your New Organ
- Kidney Function and Your New Organ
- Taking Control of Your Long-Term Health
Additional Resources
- General Transplant Organizations
- Kidney Transplant Organizations
- Organ Donation Organisations Call-To-Action Opt-In for News and Information Medication Reminder Graphic Fill out the information below and select the Submit button to receive a confirmation text message on your mobile device to get you started with mobile medication reminders. Standard message charges apply.

What's your mobile number?  ①▶ ( 949 ) 123 - 4567

What's your time zone?  ②▶ Pacific ▶

What time do you take your first dose?  ③▶ 3:00 am ▶   *A second message will be sent 12 hours later every day.*

④▶ ☐ I agree to the Terms and Conditions
       ⑤

⑥
       SUBMIT

TRANSPLANT ◀ 210

▸ Exit | Important Safety Information | Full Prescribing Information | Glossary

① Opt-In 207

> Welcome to Prograf's mobile medication reminders!
>
> You must reply "YES" to this message to start the service. After doing so, you will receive a medication twice a day at the times you selected when signing up.
>
> -------------
>
> To Opt-Out (discontinue service), text "STOP" to the short code or reply "STOP" to any message you receive.
>
> To get help, text "HELP" to the short code or email help@astellas.com or call 1-800-480-1248.

> PAGE ID: 7.1+
> PAGE TITLE: Opt-In, AM, & PM
>
> The language can be revised at any time but these are the basic messages that will appear on the user's mobile device.
>
> No artwork is involved at all, just text.
>
> NOTES:
> 1. Opt-In Message
> 2. AM Reminder
> 3. PM Reminder

② AM

> This is your morning reminder to take your Prograf medication.
>
> -------------
>
> To Opt-Out (discontinue service), text "STOP" to the short code or reply "STOP" to any message you receive.
>
> To get help, text "HELP" to the short code or email help@astellas.com or call 1-800-480-1248.

③ PM

> This is your evening reminder to take your Prograf medication.
>
> -------------
>
> To Opt-Out (discontinue service), text "STOP" to the short code or reply "STOP" to any message you receive.
>
> To get help, text "HELP" to the short code or email help@astellas.com or call 1-800-480-1248.

PAGE ID: 4.2
PAGE TITLE: Prescription Refill Reminder Setup

This page allows the user to install the Prescription Refill Reminder.

This reminder functions like a standard Time Release Message and appears on the user's desktop when the selected amount of time has passed.

A conformation page will be displayed once the application has been installed.

NOTES:
1. Standard month and day drop down menus.
2. Drop down options are limited to....
   * 30 Days
   * 60 Days
   * 90 Days
   * 6 Months
3. "Submit" button either activates the initial installation process or updates the information if it is changed later.
4. This is a new addition to the left side navigation.
5. This is a new Call-To-Action for the mobile med. reminder.

TRANSPLANT EXPERIENCE LOGO

Home
Transplant Experience
Medication Reminder
④ Prescription Refill Reminder
Educational Resources
 - Transplant Experience News
 - Sharing Life
 - Prograf and You
 - Cholesterol and Your New Organ
 - Blood Pressure and Your New Organ
 - Kidney Function and Your New Organ
 - Taking Control of Your Long-Term Health
Additional Resources
 - General Transplant Organizations
 - Kidney Transplant Organizations
 - Organ Donation Organizations Prescription Refill Reminder Graphic By filling out the information in this page, a message will automatically appear on your computer the next time your prescription is due to be refilled.

What date did you last fill your prograf prescription?

① (Month) ▸  (Day) ▸  (Year) ▸

How long does your prescription last?

② 30 Days ▸

③ SUBMIT

Call-To-Action
⑤ Opt-In for mobile medication reminders.
Standard message charges apply

TRANSPLANT

▸ Exit | Important Safety Information | Full Prescribing Information | Glossary

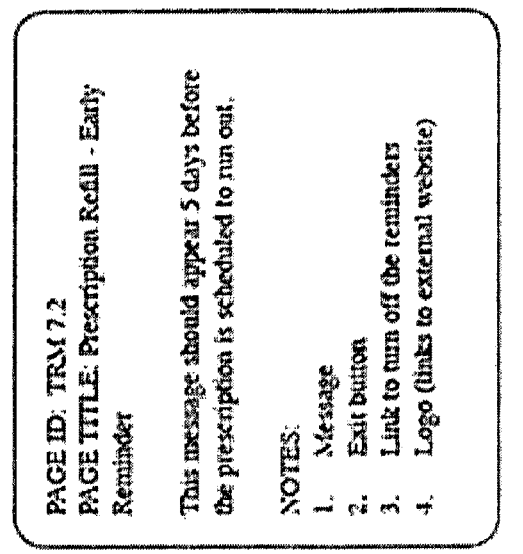
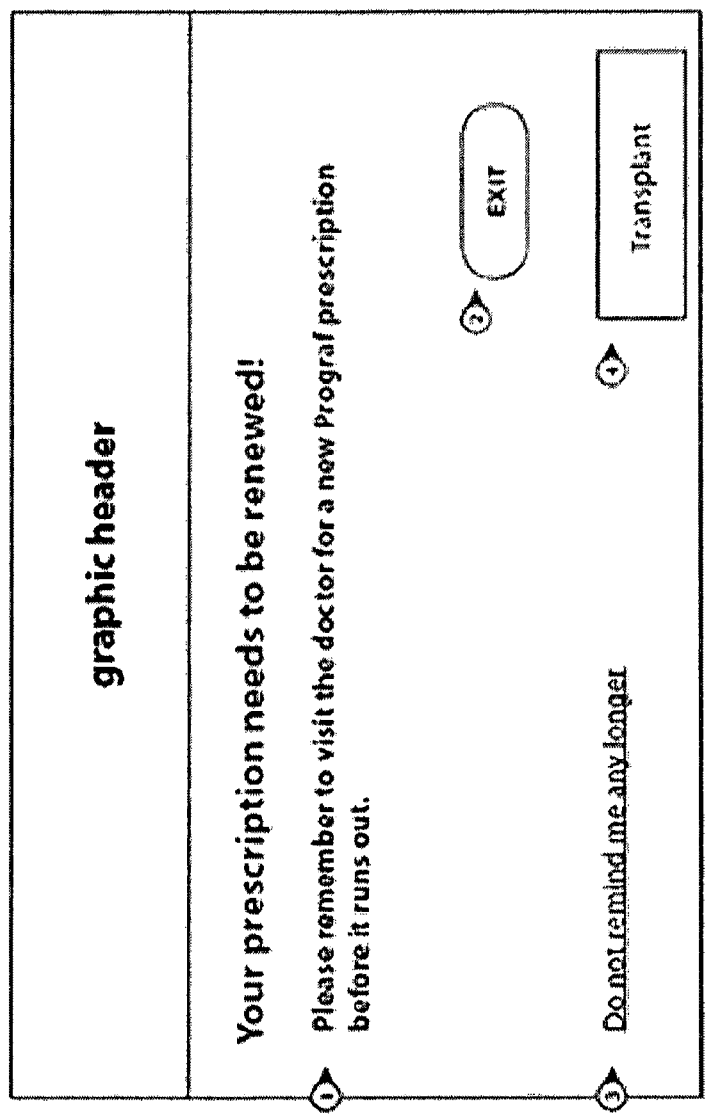
Figure 2j

7.3 215 graphic header

Have you renewed your prescription yet?

① YES  ② NO

Do not remind me any longer    Transplant

---

7.3.3 graphic header

Please remember to visit the doctor for a new Prograf prescription.

⑧ EXIT

Do not remind me any longer    Transplant

---

7.3.1 216 graphic header

Great! If you need to update the start date or the length of your prescription, please select the Update option below.

③ UPDATE  ④ EXIT

Do not remind me any longer    Transplant

---

7.3.2 graphic header

What date did you start your current prescription?
⑤ (Month) ▼ (Day) ▼ (Year) ▼
How long does your prescription last?
30 days ▼

⑥ CANCEL  ⑦ UPDATE

Do not remind me any longer    Transplant

---

PAGE ID: TRM 7.3+
PAGE TITLE: Prescription Refill Reminder

This sequence of messages appears the day before the prescription is scheduled to end and the first message will appear every day thereafter until the Yes option is selected (or "Do not remind me any longer").

NOTES:
1. Switches to 7.3.1
2. Switches to 7.3.3
3. Switches to 7.3.2
4. Closes the message and leaves the schedule for the next reminder at the same settings with a new start date automatically set.
5. The fields can be filled in with the pre-determined new start date and the same duration.
6. Closes the message without making any changes other than a reset to the new start date.
7. Closes the message and any changes are saved for the next TRM delivery.
8. Closes the window and sets a flag for 7.3 to appear again the next day.

Figure 2k

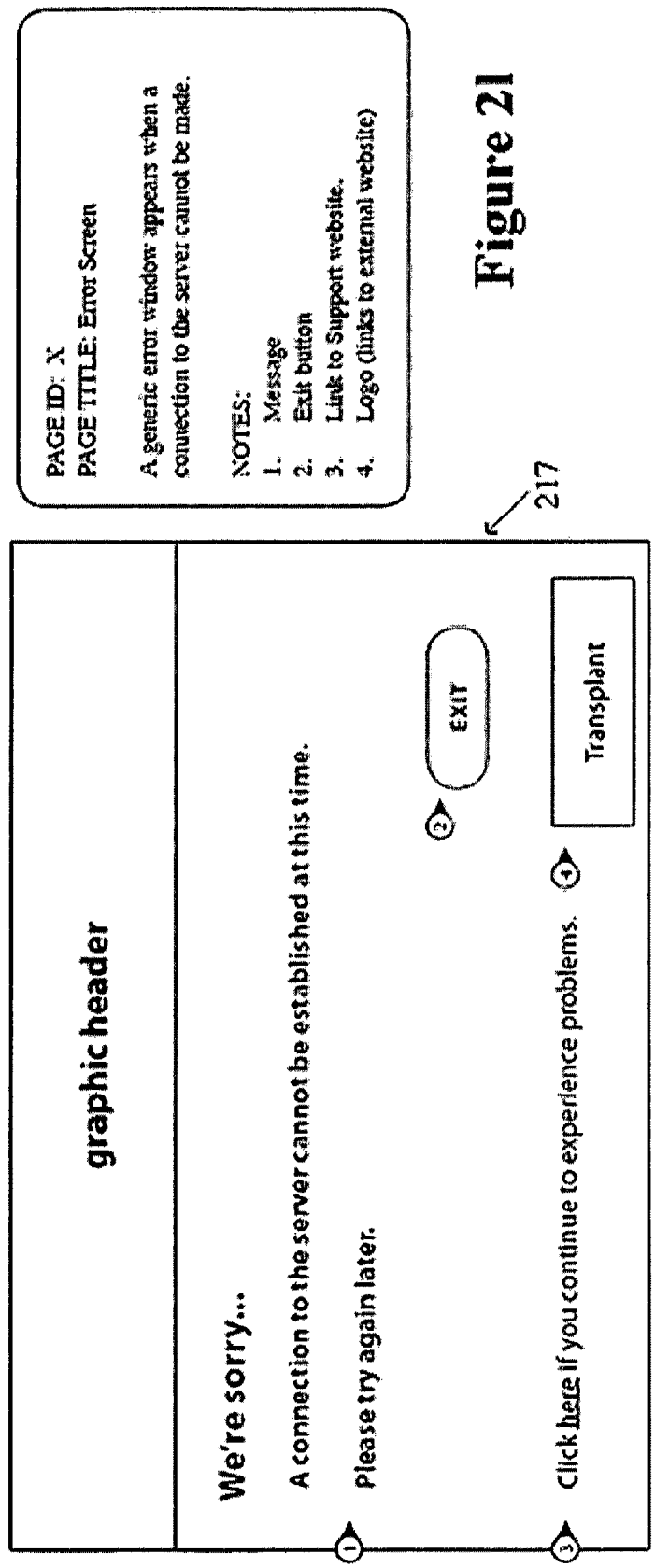

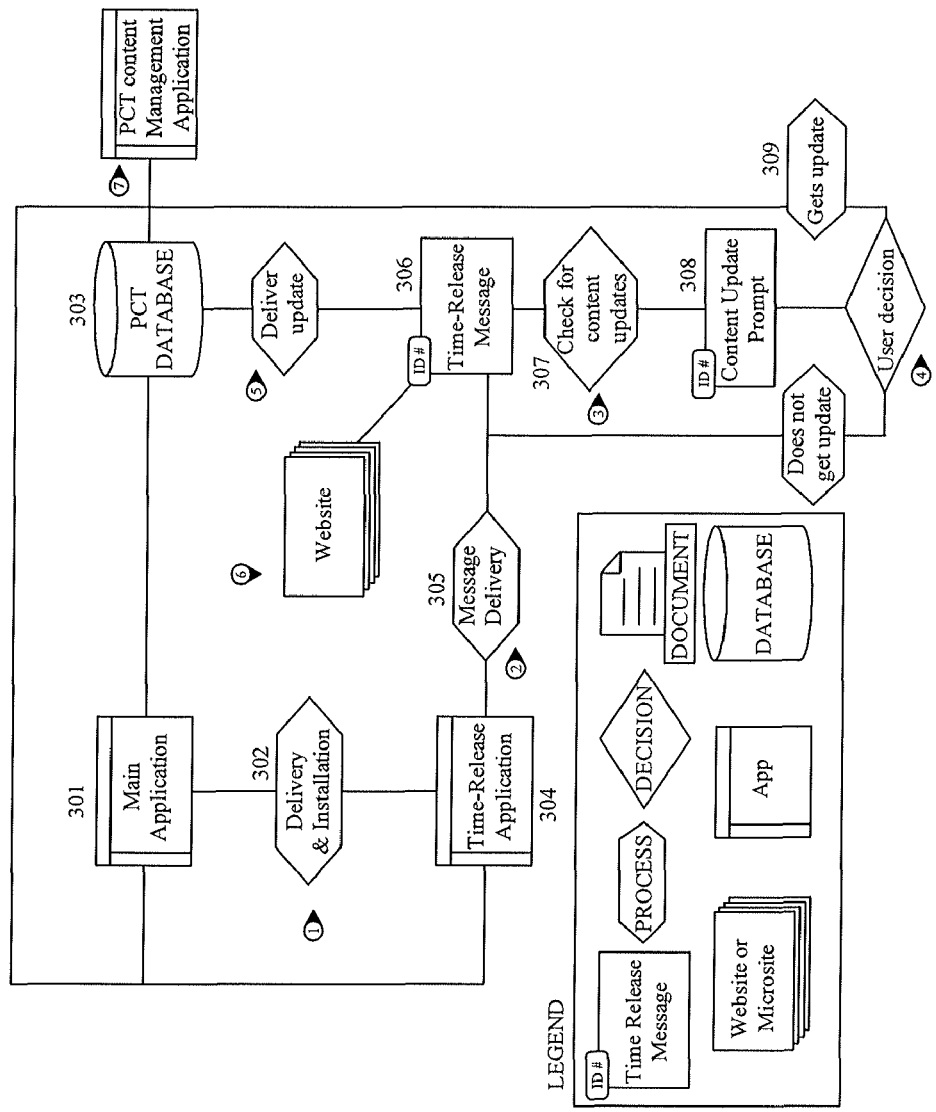

Figure 3

This page describes the general process of the delivery and functions of Time-Release Messaging.

1. The user interacts with a main application, opts-in to receive Time-Release Messaging and then the Time-Release Message application is installed.
2. Messages are delivered relative to the first use of the installation of the Time-Release application or at predetermined dates and times.
3. When a Time-Release Message is delivered to the user's desktop, it checks for updates by querying a database containing content related to the Time Release Message content. If updates are available, the application prompts the user letting them know an update is available.
4. The user decides whether or not to download the content update. If the user does not get the content update, then the original Time-Release Message is displayed. If the user decides to get the update, the application checks the PCT database to download the content update.
5. The content update is delivered to the user as a download and a new message appears.
6. Users can on links to websites within the Time-Release Message application and be automatically directed to the corresponding websites.
7. The Content Management System allows administrative management of the content contained within the Time-Release Messages. It also allows the administrator to change the timing of message delivery.

PERSONALIZED TIME RELEASE MESSAGING

CROSS REFERENCE TO RELATED APPLICATIONS

This application is related to, claims priority from, and incorporates by reference in their entirety, provisional patent applications 61/122,611, entitled Personalized Time Release Messaging, filed on Dec. 15, 2008, and 61/119,183, entitled Loyalty Text and Personalized CD System and Method, filed on Dec. 2, 2008, both of which list Robert Charles Morton as their sole inventor.

INCORPORATION BY REFERENCE

This application incorporates by reference in its entirety the information from the computer program listing appendix submitted herewith, comprising the files listed in the table below:

| Date | Size | Name |
|---|---|---|
| Directory of d:\client | | |
| Nov. 5, 2009 10:39a | 10,371 | Reminder.as |
| Nov. 20, 2009 11:28a | 1,161 | TimeRelease.sql |
| Directory of d:\client\pct | | |
| Sep. 22, 2009 01:42p | 1,953 | BasicButton.as |
| Oct. 28, 2009 12:21p | 3,011 | GUID.as |
| Nov. 9, 2009 03:50p | 10,650 | PDFviewer.as |
| Nov. 9, 2009 03:49p | 8,247 | Playback.as |
| Aug. 24, 2009 09:59a | 1,644 | RhythmMail.as |
| Nov. 5, 2009 01:52p | 9,387 | Settings.as |
| Nov. 2, 2009 04:50p | 13,554 | TimeRelease.as |
| Oct. 29, 2009 04:10p | 747 | TimeReleaseEvent.as |
| Aug. 31, 2009 03:46p | 907 | ToolbarButton.as |
| Aug. 31, 2009 02:09p | 5,298 | ToolTip.as |
| Oct. 30, 2009 03:22p | 7,971 | Tracking.as |
| Aug. 20, 2009 12:59p | 1,035 | UpdateEvent.as |
| Directory of d:\server | | |
| Nov. 20, 2009 11:26a | 418 | events.sql |
| Nov. 20, 2009 11:25a | 2,258 | gettimerelease.php |
| Nov. 20, 2009 11:30a | 179 | mysql_connect.php | on the compact discs submitted herewith, and the computer program which is represented by their combination. Two identical discs, each containing the files listed above are submitted herewith.

BACKGROUND

Research has shown that only 15% of patients understand what their doctors tell them, and that about 50% of patients leave their physician's office uncertain as to the next steps in their diagnosis and/or their treatment options. In cases where a patient leaves a physician's office with a prescription, one in five will never fill that prescription at a pharmacy. Accordingly, there is a substantial need for improved technology which can be used to facilitate transfer of information to patients, for technology which can help support patient compliance with treatment programs. Additionally, in light of the generally poor performance of existing technologies, there is a need for technology which can allow monitoring of patient communication and/or compliance activities, and which can be modified after deployment to improve effectiveness.

SUMMARY

Aspects of the technology disclosed herein can be used in a variety of implementations which can provide benefits such as improved communication and compliance with patient treatment programs. For example, using the technology disclosed herein, one of ordinary skill in the art could create computer readable media which can configure a computer to perform tasks such as enrolling a user in a compliance assistance program, presenting messages according to a presentation schedule, modifying the presentation schedule according to modifications received from a remote server, and storing data reflecting a user's access to information. Similarly, the technology described herein could be used to implement a computer configured to perform tasks such as receiving an indication of a user's enrollment in a time release messaging program, a mobile phone number for the user, a prescription refill schedule for the user, and an identification code for a media device provided to the user. Such a computer could also be configured to send a message to the mobile phone number for the user indicating that a prescription should be refilled based on the physical proximity of a mobile device associated with the user's phone number to a pharmacy, and temporal proximity of a date when the prescription refill schedule indicates that a prescription should be refilled.

Of course, the technology disclosed herein is also amenable to implementation in forms other than computer readable media and computers as described above. For example, various methods, machines, and articles of manufacture are both contemplated by the inventors, and could be implemented by those of ordinary skill in the art without undue experimentation in light of this disclosure. Accordingly, the summary above, as well as the disclosure set forth herein, should be understood as being illustrative only, and not limiting.

BRIEF DESCRIPTION OF THE DRAWINGS

The drawings and detailed description which follow are intended to be merely illustrative and are not intended to limit the scope of the invention as contemplated by the inventors.

FIG. 1 depicts an example of a method which utilizes media device distribution.

FIGS. 2a-2l indicate how information and messaging could be provided through an enhanced CD.

FIG. 3 depicts potential processes and components which could be used in implementing time release messaging.

DETAILED DESCRIPTION

Figure 2A:
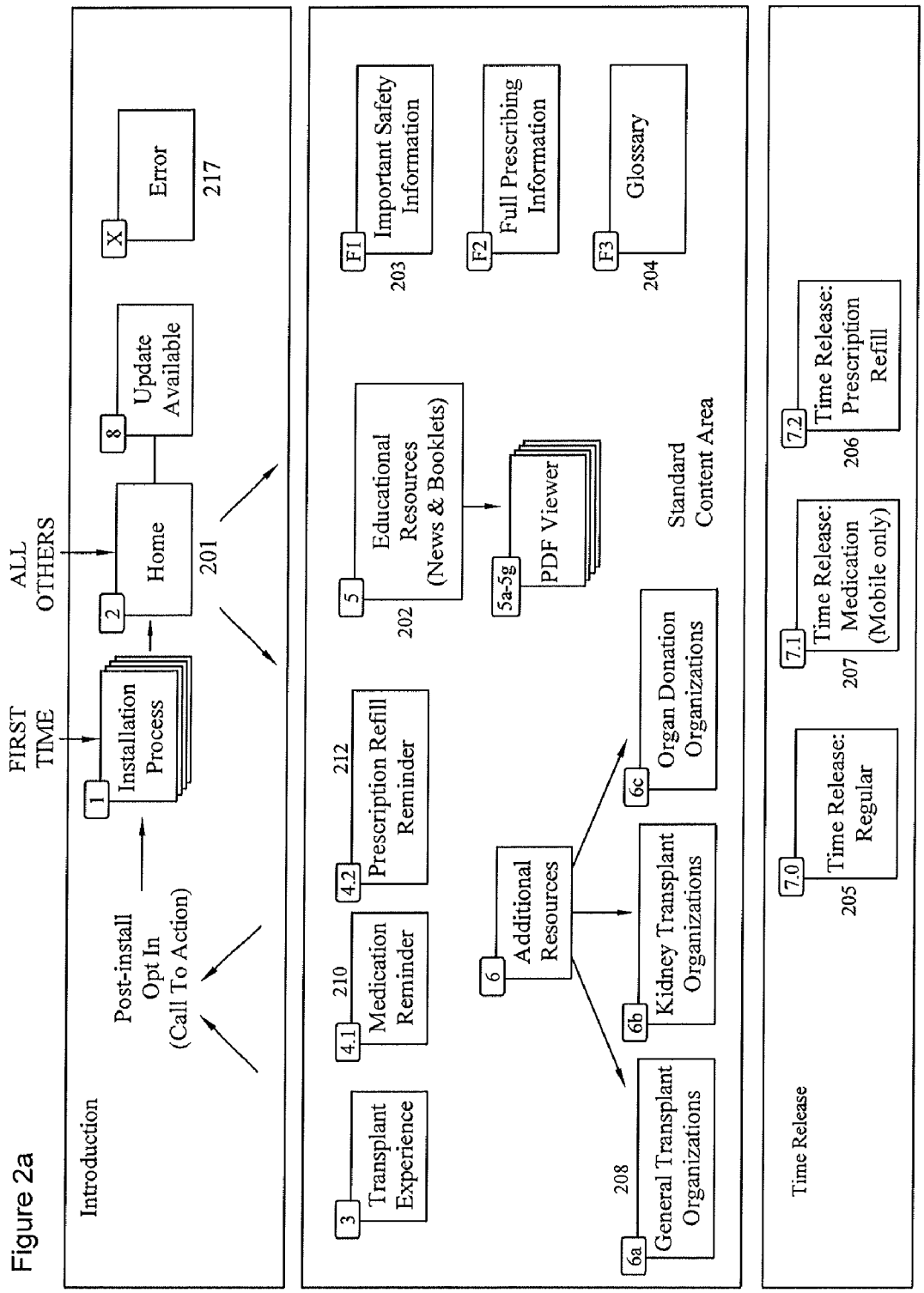

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

The inventors have conceived of novel technology which, for the purpose of illustration, is disclosed herein as applied to the context of supporting patient communication and treatment compliance. While application of the inventors' technology in that context satisfies a long-felt but unmet need in the art, the disclosure of the inventors' technology in that context should not be treated as implying limitations on potential fields where aspects of the inventors' technology can be beneficially applied. Accordingly, the disclosure set forth herein should be understood as being illustrative only, and not limiting.

As set forth herein, it is possible that patient communication and/or treatment compliance could be supported through the use of media devices (e.g., compact discs) which are distributed to patients. An example of a method which utilizes this type of media device distribution is illustrated in FIG. 1. Initially, in the method of FIG. 1, compact discs with information specific to a particular pharmaceutical which could be prescribed (referred to as ECDs, or enhanced CDs) are distributed to doctors who could write prescriptions [101]. These discs could be distributed in finished form (e.g., multiple discs given to each doctor), could be distributed in master form (e.g., each doctor would be given a master disc, which could be used to make copies as needed using equipment at the doctor's office), could be distributed in download form (e.g., doctors could be given access to a web site where they could download information that could be used to create the CDs) or in some other manner. As shown in FIG. 1, the discs could be distributed by sales representatives, such as representatives of the company which makes the pharmaceutical which is the subject of the ECD, thereby providing physicians access to the ECDs at no additional charge. Similarly, as shown in FIG. 1, it is possible that disc distribution could be targeted, such as by only distributing ECDs to physicians in the top decile with respect to prescriptions written, or by distributing ECDs selectively based on the number of patients seen by an individual doctor. Of course, it should be understood that targeted distribution by sales representatives such as described above is intended to be exemplary, and should not be treated as limiting on how ECDs could be distributed. For example, ECDs could be sent via direct mail based on databases of physician information, they could be distributed as part of corporate health insurance enrollments, they could be distributed or provided as samples at wellness clinics, made available in response to requests (e.g., submitted through a web site), or using other approaches which might be appropriate in a given scenario.

Once the ECDs had been distributed, when a doctor diagnoses a patient as having a condition treatable with the pharmaceutical which is the subject of the ECD, the patient could be given, in addition to a prescription for the pharmaceutical, a copy of the relevant ECD [102]. Further, as shown in FIG. 1, when the ECD is provided to the patient [102] either the doctor or some member of his or her staff (or both) could explain how the ECD could benefit the patient. For example, the patient could be told that the ECD could provide hours of defined and relevant information regarding the patient's disease state and prescription, which the patient could view in his or her own home at his or her own pace. Additionally, in implementations where an ECD is also configured with time release messaging (e.g., periodic reminder and compliance assistance functionality such as discussed herein) the benefits of that technology could also be discussed when the ECD is given to the patient [102]. This could not only help ensure that the patient is aware of (and likely to use) the information and support functionality from the ECD, but could also allow the physician to spend more time on treatment and diagnosis, and less time having to provide (and explain) information included on the ECD.

After the ECD has been given to the patient [102], the patient could use the ECD, such as by putting it into his or her computer [103]. This could result in, once the patient agrees to a set of terms and conditions, enrolling the patient in a compliance assistance program, such as the Loyalty Text program mentioned in FIG. 1. In some implementations, even if the patient chooses not to enroll in the Loyalty Text program, he or she could still use the ECD to review information on his or her prescription, such as side effects, expected benefits, dosage schedule, or other material which might be appropriate in a given case. Alternatively, if the patient had enrolled in the Loyalty Text (or other compliance assistance program), he or she could be prompted to enter the date the prescription should first be filled. Subsequently, reminders to refill the prescription could be generated at appropriate times and presented to the patient (e.g., displayed on the patient's desktop). Once the reminder has been sent (or once the time to refill a prescription approaches, in the event that a reminder was not sent to the patient) the patent's location could be tracked [105] (e.g., via GPS or cell phone triangulation given the mobile number supplied previously) and a compliance assistance message could be generated [106] and sent to the patient [107] when the patient enters the proximity of his or her local pharmacy. The compliance assistance message could take a variety of forms. For example, it could simply be a text message drawing the patient's attention to his or her proximity to the pharmacy, it could provide instructions for the patient on how to reach the pharmacy from his or her current location, it could provide information on the prescription itself, or the patient's method of payment, or it could provide other data as might be appropriate in certain instances. Indeed, in some instances, the compliance assistance message could contain no information at all, such as in a case where the patient's mobile phone is programmed with a special ringtone designated as indicating proximity to a pharmacy, and the compliance assistance message comprises a phone call from a number associated with that ringtone. Accordingly, the discussion above related to messaging for the patient, and various types of compliance assistance messages, should be understood as being illustrative only, and not limiting.

Additionally, as shown in FIG. 1, in some cases, the technology disclosed herein could be used once the patient had entered a pharmacy to refill his or her prescription. For example, in cases where a compliance assistance message containing information about the patient's co-pays or discounts had been sent to the patient, a pharmacist could scan (in the event the compliance assistance message had included a barcode or some other machine readable data), or enter data from, the compliance assistance message to facilitate adjudication [108]. The adjudication could then take place [109], and the process could be reset, so that a new message could be sent (and/or other steps performed) the next time the patient's prescription needed to be refilled.

As a further example of how a method such as discussed with respect to FIG. 1 could be implemented, FIGS. 2a-2l indicate how information and compliance assistance messaging could be provided through an enhanced CD. FIG. 2a shows how, in an exemplary embodiment in which information on an enhanced CD is organized into pages, those pages could be presented to a patient. As shown in FIG. 2a, an enhanced CD could include a home page [201] which could be presented to a patient when he or she indicates a desire to use the enhanced CD, and which might include links to other pages (or other ways of indicating a desire to view other pages, such as buttons, menus, etc), such as educational resources [202], safety information, [203], and a glossary [204]. Also, as shown in FIG. 2a, the enhanced CD could include pages related to time release messaging (or some other type of compliance assistance program) such as a regular time release messaging page [205], or a time release prescription refill page [206]. Also, as shown in FIG. 2a, the information on the ECD could be integrated with information that is external to the ECD itself. For example, the ECD could be used to set up a time release messaging program which would send mobile only reminders [207] to a phone or other mobile device. Similarly, the enhanced CD could have links to external pages, such as general transplant organizations in the event that the ECD was created for distribution to patients who had recently had (or were contemplating) a transplant. The enhanced CD could also have pages designed to be invoked when external information is not available, such as an error page [217] of the type shown in FIG. 2l, which could be shown when a user selects external content (or a connection to an external resource is otherwise called for) and that external content is not available (e.g., due to remote server or network connection failure).

Figure 2B:
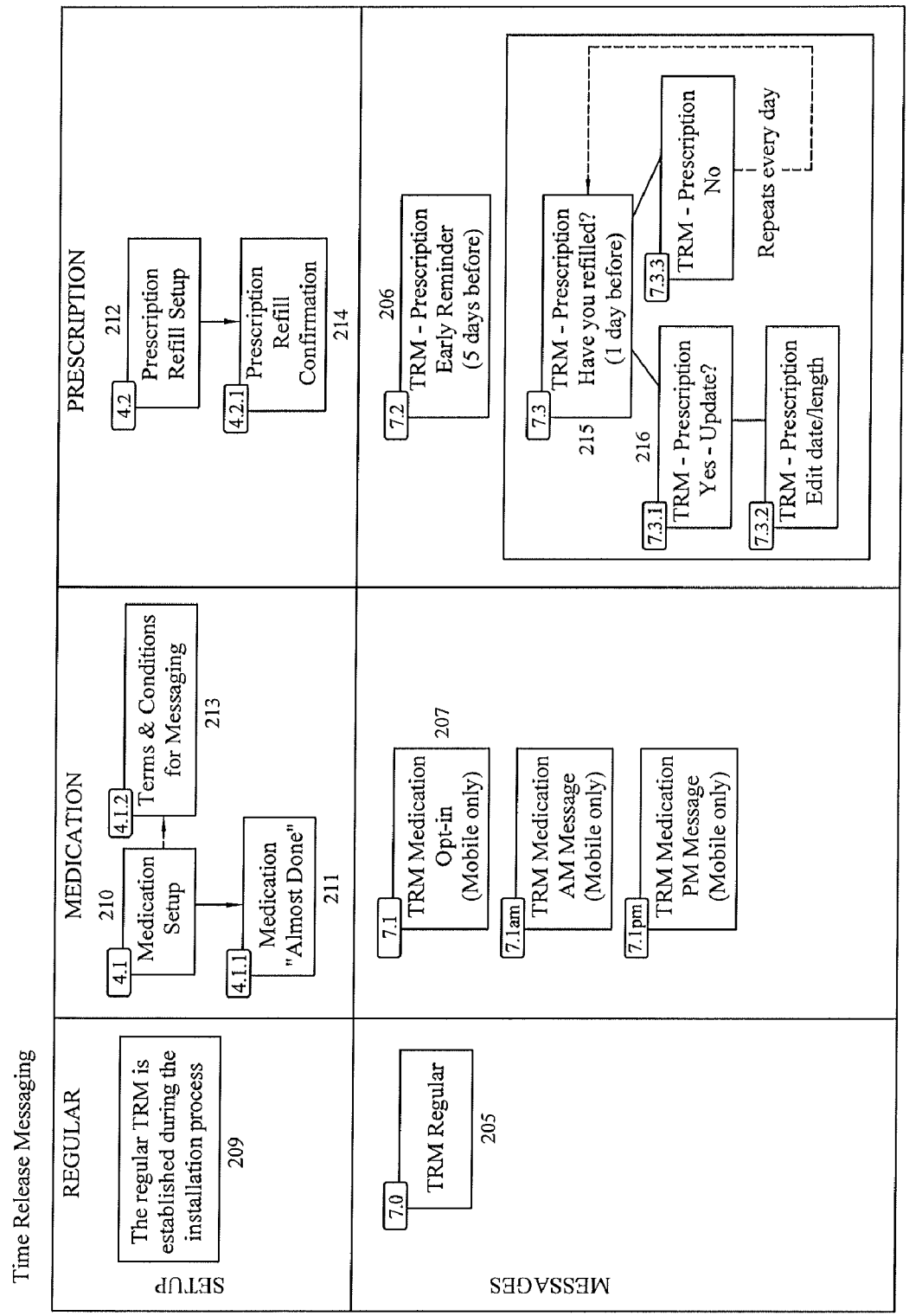
Figure 2E:
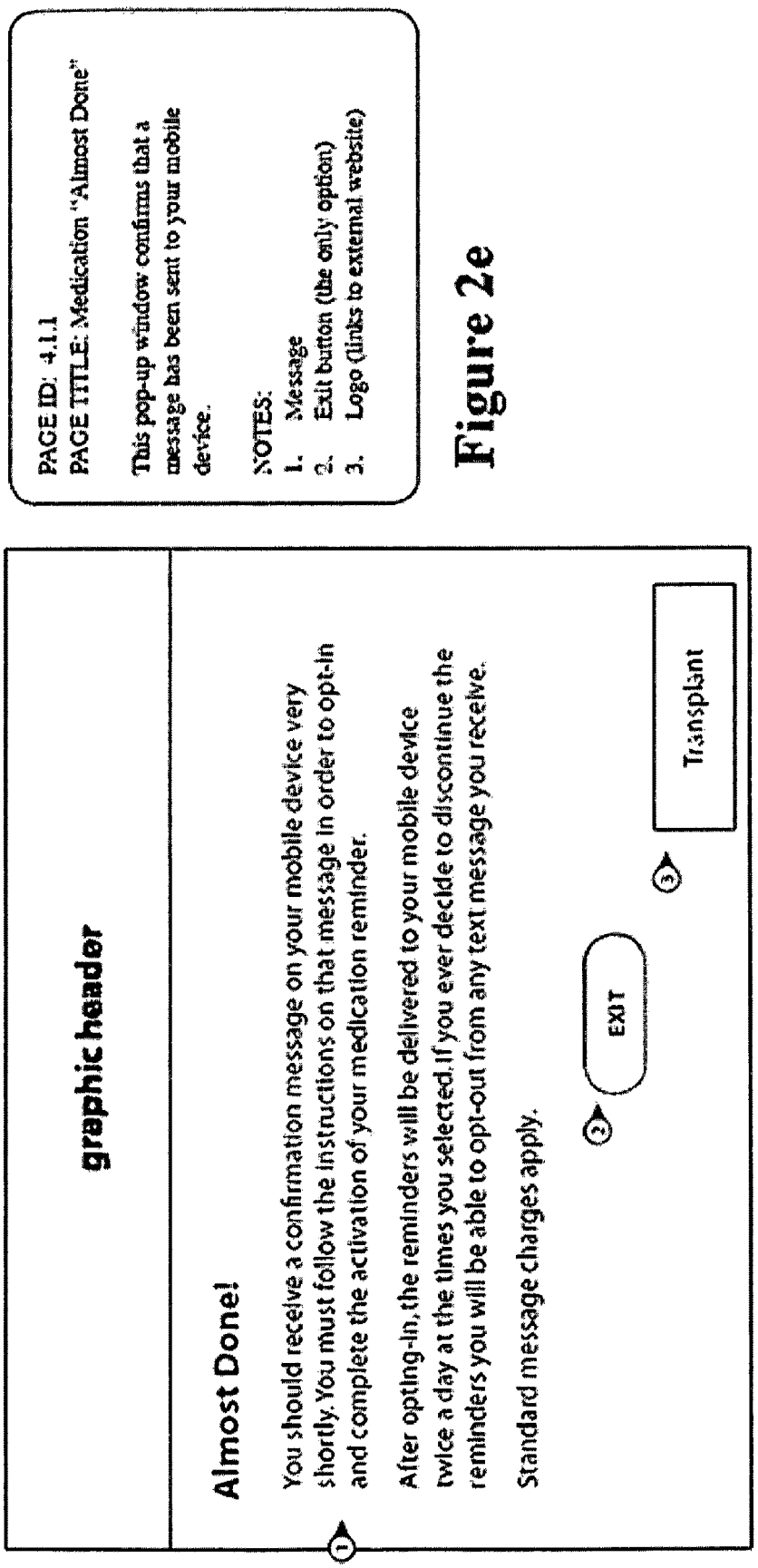
Figure 2F:
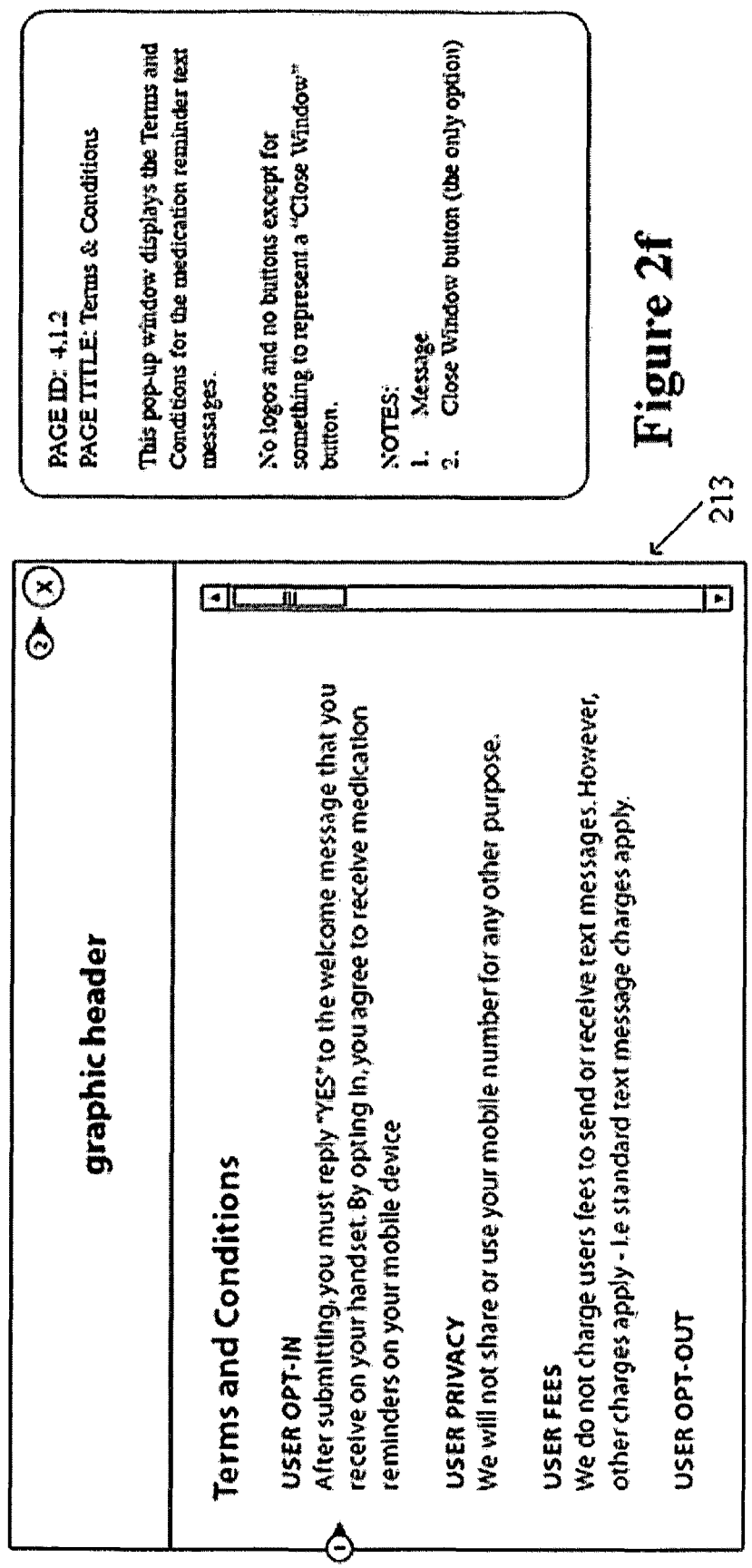
Figure 2I:
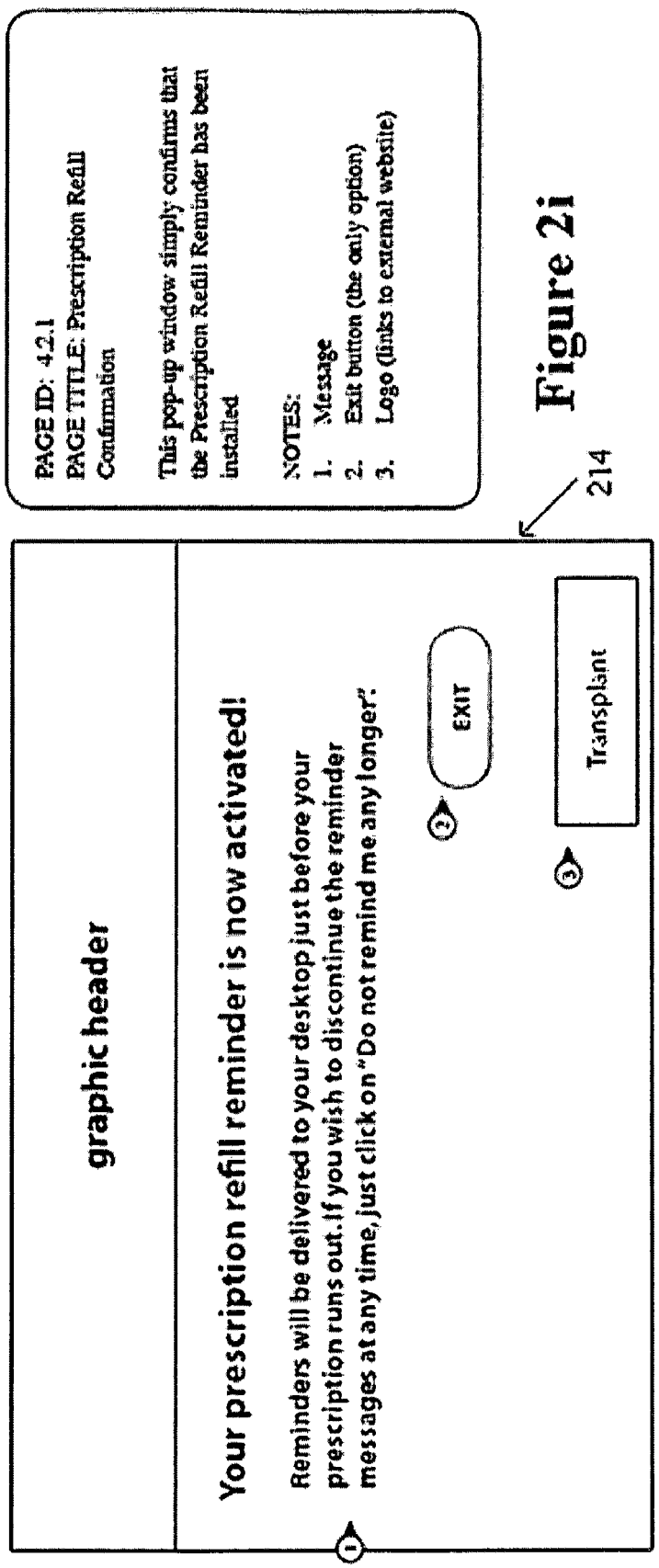

Turning now to FIG. 2b, that figure shows, in implementations in which an enhanced CD is used in conjunction with a time release messaging program, how the time release messaging information could be structured and presented to a patient. As shown in FIG. 2b, there could be two distinct aspects to this: setup, and messaging. The setup aspect could include gathering of basic information from a user using a basic TRM setup page [209], and could also allow the user to perform actions such as opting out of time release messaging, or choosing to set up the time release messaging program at a later date. The setup aspect could also be structured to allow the user to set up different parts of a time release messaging program. For example, as shown in FIG. 2b, a time release messaging program could be structured to provide medication reminders (i.e., reminder messages reminding a user to take a prescription on schedule), and prescription refill reminders (i.e., reminder messages reminding a user to refill a prescription), and there could be separate pages for setting up each type of reminder. For medication reminders, there could be a medication reminder setup page [210], shown in both FIGS. 2a and 2b, with an exemplary format set forth in FIG. 2d. The message setup might also include a penultimate page [211], indicating that the message setup is almost complete, an example of which is set forth in FIG. 2e, and a terms and conditions page [213] (an example of which is set forth in FIG. 2o, showing information such as privacy information, opt in information, or fees. For prescription refill reminders, there could be a prescription refill reminder setup page [212], shown in both FIGS. 2a and 2b, with an exemplary format set forth in FIG. 2h. There could also be a prescription refill confirmation page [214], such as might have the exemplary format shown in FIG. 2i. As shown in FIG. 2a, these setup messages could be shown to a user when he or she first activates the enhanced CD, or could be shown later on, for example if a user initially decides to opt out of a time release messaging program (or some aspect of that program) and later decides to opt in.

In addition to the setup information for time release messaging, there could also be the actual messages themselves, which, as shown in FIG. 2b, could be conceptualized as being regular messages, prescription messages, or medication messages. The regular messages [205] could be used for a variety of purposes, such as allowing the entity which sponsored or created the enhanced CD to provide additional information to the user, allow the user to opt out of the time release messaging program, or to provide links to external (or internal) sites. An exemplary format for such a regular message is shown in FIG. 2c. There could also be specialized messages for medication [207] and prescription [206] reminders. As shown in the exemplary format of FIG. 2g, the medication reminders could include opt in messages [207], as well as custom messages for morning and evening medication doses. The prescription reminders could include an early reminder message [206] (an exemplary format for which is shown in FIG. 2j), as well as reminders which could be provided closer to (or even after) the time the prescription was to be filed. As shown in FIG. 2b, these subsequent reminders could be programmed to be presented in a cycle, with an imminent reminder message [215] being shown on a daily basis starting one day before the prescription is refilled, and continuing until the refill actually takes place. Once the prescription has been filled (or, in some implementations, as an alternative to filling the prescription), a user could change his or her refill schedule using an update page [216]. Exemplary formats for such an update page, as well as for other pages which could be provided as part of the prescription refill reminders are shown in FIG. 2k.

Turning now to FIG. 3, that figure presents additional information regarding potential approaches to implementing time release messaging. As shown in FIG. 3, time release messaging could be implemented through a main application [301]. This main application could be configured to run automatically the first time a patient uses an enhanced CD, periodically, on user request (e.g., if the user who initially opts out of the program decides later to participate), or based on some other type of trigger. This main application could provide the user the opportunity to opt in to the time release messaging program, and, if the user decides to opt in, could trigger a delivery and installation process [302]. This delivery and installation process could be used to transfer information (e.g., content such as described with respect to FIGS. 2a-2l, instructions for supporting reminder functionality, etc) from the enhanced CD to the hard drive of the user's computer, so that the enhanced CD's functionality could be provided even if the enhanced CD is not available. Similarly, the delivery and installation process could query a remote database (e.g., PCT database, [303]) to retrieve content which might not have been included on the enhanced CD and/or to update content which was included on the enhanced CD but which might require some modification. One type of information which could be transferred to the user's hard drive during the delivery and installation process [302] is a time release messaging application [304], which could be configured to automatically cause the delivery of messages [305], and/or to perform updating functions. The delivery of messages could be implemented as described previously with respect to FIGS. 2a-2l, but also could include other types of message delivery, such as delivery of messages regarding newly discovered risks/benefits to a particular medication, or delivery of messages regarding other treatments or pharmaceuticals which could potentially benefit a patient to whom an enhanced CD had been distributed.

In addition to the delivery of messages as described above, a time release application [304] could also be used to update content which could be presented to a user, and/or to change the timing of messages. This could be done by, when a message [306] is provided to a user, querying [307] a database [303] to determine if there are any updates related to the message being provided. If there are, the user could be prompted [308] as to whether or not he or she wanted to get the update, and, if so, the update could be downloaded [309] and an updated message could be provided to the user. Of course, implementations in which updating is performed independently of message delivery are also possible. For example, the time release application [304] could be programmed to periodically check the database [303] for updates, whether or not a message is being provided. Similarly, a time release application [304] could be configured to receive messages indicating that an update is available, and could query for updates upon receipt of the messages as opposed to (or in addition to) updating when providing messages to a user, or on a periodic schedule. In terms of the actual content of updates, a system implemented as shown in FIG. 3 could be configured to support a variety of update types, including updates which change the content of existing messages (e.g., by adding new text, images, PDF files, videos, games, or other types of media, potentially in combination with removal of media which had previously been included in the messages), and updates which provide entirely new messages. It is also possible that a system implemented as shown in FIG. 3 could support updates which do not modify the messages presented to users at all. For example, there could be an update which would state that a message which was previously presented to a user on a monthly basis should instead be presented every two weeks, thereby changing the message's timing, but not its content. Other types of updates (e.g., updates to the software to add additional features, such as new types of security) are also possible, and their application to technology such as described herein will be immediately apparent to those of ordinary skill in the art. Accordingly, the discussion of updating, as well as the related discussion of message delivery, should be understood as being illustrative only, and not limiting.

It should be understood that the discussion of variations on potential approaches to updating and time release messaging set forth above are not intended to imply that either updating, or time release messaging, is a required element of an enhanced CD. For example, in some cases, as an alternative to time release messaging, an enhanced CD could include personalization features which could be customized with respect to doctors who would distribute the enhanced CDs to patients. As a concrete illustration of how this could take place, consider a scenario in which ECDs are targeted for doctors who write substantial numbers of prescriptions, and are distributed to those doctors by sales representatives. In this scenario, the sales representatives could invite the relevant doctors to record a short message which could be used as an introduction to the ECD. These messages could then be stored on the ECDs and given to the doctors. When the doctors provided the ECDs to patients, they could also provide a code linking the ECD with the doctor who provided it. When the patient uses the ECD, he or she could enter the code, which would result in the appropriate doctor video being retrieved from the ECD and being played for the patient. This could be done by creating different customized ECDs for each doctor, by creating a single ECD with all doctor videos (and retrieving the correct video based on the code), or by some other means. For example, the videos could be stored on a networked server, and when the code was entered, it would be communicated to the networked server which would provide the proper video to the patient's desktop (alternatively, if no connection was available, a default video would play). Of course, while the personalization functionality described above was presented as an alternative to time release messaging, it is possible that a single enhanced CD could provide both personalization and time release messaging, and that the description of those functionalities as alternatives was intended to demonstrate that the inventors' technology was not limited to implementations in which time release messaging is present.

As a further illustration of how aspects of the inventors' technology could potentially implemented, consider the computer program appendix submitted herewith, which is incorporated herein by reference in its entirety. That code, when used to configure a computer (or multiple computers, depending on the architecture of a particular system), could cause the computer to perform certain aspects of the messaging, and updating functionality set forth herein. Additionally, that computer program appendix includes code which could configure a computer to support tracking of user activities, which code, as well as the code supporting updating, is licensed from Point-Click Technology, LLC. It should be understood that other code could potentially be used to support those features (including independently developed code), and that the technology disclosed herein is not limited to being implemented using code licensed from those (or any other) entities. However, it should also be understood that, by providing the computer program appendix, neither the inventors nor their licensors grant any right or license to any third party to copy that code for any purpose, with the exception of copies consistent with the copyright or mask work notice set forth herein.

Of course, the computer program listing appendix, like the remainder of this disclosure, should be understood as being illustrative of the inventors' technology, and should not be treated as implying limits on how that technology could potentially be applied. Indeed, other applications and implementations of the disclosed technology are contemplated by the inventors and will be immediately apparent to one of ordinary skill in the art in light of this disclosure. For example, the disclosure above focused on potential applications of the inventors' technology in the context of enhanced CDs. However, it is equally possible that other types of media devices, such as DVD-ROM or USB thumb drive could be used in place of compact discs, or even that no media devices would be distributed at all, as might be the case in scenarios where software and/or content are provided via download. Accordingly, instead of limiting the protection accorded by this document, or by any document which is related to this document, to the material explicitly disclosed herein, the protection should be understood to be defined by the following claims, which are drafted to reflect the scope of protection sought by the inventors in this document when the terms in those claims which are listed below under the label "Explicit Definitions" are given the explicit definitions set forth therein, and the remaining terms are given their broadest reasonable interpretation as shown by a general purpose dictionary. To the extent that the interpretation which would be given to the claims based on the above disclosure or the incorporated priority documents is in any way narrower than the interpretation which would be given based on the "Explicit Definitions" and the broadest reasonable interpretation as provided by a general purpose dictionary, the interpretation provided by the "Explicit Definitions" and broadest reasonable interpretation as provided by a general purpose dictionary shall control, and the inconsistent usage of terms in the specification or priority documents shall have no effect.

EXPLICIT DEFINITIONS

When used in the claims, "adjudicate a claim for the refill" should be understood to refer to processing a request for payment for the refill, such as by determining if the refill is covered by an insurance carrier, and what (if any) co-pay is required for the refill.

When used in the claims, "anonymous data" should be understood to mean data which is not explicitly correlated with any particular individual. For example, data which stated that a program was accessed a certain number of times, but which did not state who accessed the program, would be considered "anonymous data."

When used in the claims, "based on" should be understood to mean that something is determined at least in part by the thing that it is indicated as being "based on." When something is completely determined by a thing, it will be described as being "based EXCLUSIVELY on" the thing.

When used in the claims, "computer" should be understood to mean a device or group of devices which is capable of performing one or more logical and/or physical operations on data to produce a result.

When used in the claims, "computer readable medium" should be understood to mean any object, substance, or combination of objects or substances, capable of storing data or instructions in a form in which they can be retrieved and/or processed by a device. A computer readable medium should not be limited to any particular type or organization, and should be understood to include distributed and decentralized systems however they are physically or logically disposed, as well as storage objects of systems which are located in a defined and/or circumscribed physical and/or logical space.

When used in the claims, to "configure" a computer should be understood to mean providing the computer with specific data (which may include instructions) which can be used in performing the specific acts the computer is being "configured" to do. For example, installing Microsoft WORD on a computer "configures" that computer to function as a word processor, which it does using the instructions for Microsoft WORD in combination with other inputs, such as an operating system, and various peripherals (e.g., a keyboard, monitor, etc. . . . ).

When used in the claims, "period" should be understood to refer to a specified division or length of time.

When used in the claims, a statement that an computer is "remote" from another computer should be understood to mean that communication between the computers takes place over a network, such as a wide area network, a local area network, or a sneakernet.

When used in the claims, "server" should be understood to refer to a computer which is connected to a network and configured to receive requests from other computers.

We claim:

1. A non-transitory computer readable medium, having stored thereon a set of instructions operable to configure a computer to perform a set of tasks comprising:
   a) sending, to a remote server, a signal indicating enrollment of a user of the computer in a patient assistance program;
   b) installing, from the non-transitory computer readable medium to a memory of the computer:
      i) a message, the message comprising a content element;
      ii) a presentation schedule comprising a period;
   c) presenting the message to the user via displaying the message on a display device of the computer, wherein the message is presented according to the presentation schedule, wherein presenting the message according to the presentation schedule comprises presenting the message:
      i) during a first time period, wherein the first time period starts with enrollment of the user in the patient assistance program and has a duration equal to the period from the presentation schedule;
      ii) during each of a plurality of subsequent time periods, wherein each of the subsequent time periods starts with a previous presentation of the message, and has a duration equal to the period from the presentation schedule;
   d) based on receiving a period modification from the remote server, modifying the presentation schedule stored in the computer to change the period from the presentation schedule;
   e) based on receiving a content modification from the remote server, modifying the message stored in the computer to change the content element from the message;
   f) making a request for an identification code provided to the user and linked to a prescribing physician from whom a prescription for a pharmaceutical product was provided to the user;
   g) in response to receiving the identification code, presenting a video segment in which the prescribing physician was recorded;
   wherein:
   A) the video segment in which the prescribing physician was recorded is a video segment from a plurality of video segments stored on the non-transitory computer readable medium;
   B) the plurality of video segments comprises a set of physician video segments featuring physicians other than the prescribing physician;
   C) each physician video segment from the set of video segments corresponds to a physician identification code linked to the physician other than the prescribing physician featured in the other physician video segment; and
   D) the set of tasks the instructions stored on the non-transitory computer readable medium is operable to configure the computer to perform comprises:
      I) in response to receiving a physician identification code linked to a physician other than the prescribing physician featured in a physician video segment, retrieving the physician video segment featuring the physician other than the prescribing physician.

2. The computer readable medium of claim 1, wherein the set of tasks comprises:
   a) receiving a prescription refill schedule from the user;
   b) storing the prescription refill schedule on the memory of the computer;
   c) determining a first date for providing an early prescription refill reminder, wherein the first date is determined based on identifying a date which precedes a date on which the prescription refill schedule indicates a refill should take place by a first time period;
   d) providing the early prescription refill reminder on the first date;
   e) determining a second date for providing a proximate prescription refill reminder, wherein the second date is determined based on identifying a date which precedes the date on which the prescription refill schedule indicates the refill should take place by less than the first time period;
   f) providing the proximate prescription refill reminder on the second date;
   g) receiving an indication that the prescription has been refilled; and
   h) if the indication that the prescription has been refilled is received after the proximate prescription refill reminder is provided on the second date, periodically providing additional prescription refill reminders between the provision of the proximate prescription refill reminder, and the receipt of the indication that the prescription has been refilled.

3. The computer readable medium of claim 1, wherein the set of tasks comprises:
   a) receiving a dosage schedule from the user;
   b) storing the dosage schedule on the memory of the computer;
   c) determining a time for providing a medication reminder, wherein the time is determined based on identifying a time which precedes a time when the dosage schedule indicates that the user should take the medication; and
   d) providing the medication reminder on the determined time.

4. The computer readable medium of claim 1, wherein the set of tasks comprises:
 a) requesting that the user provide an identification code associated with the computer readable medium;
 b) in response to receiving the identification code, retrieving a video of a physician associated with said user; and
 c) presenting, as an alternative to a default video, the video of the physician associated with the user.

5. The computer readable medium of claim 1 wherein:
 a) the computer readable medium is a tangible computer readable medium adapted for insertion into the computer; and
 b) the set of instructions are operable to configure the computer to perform the set of tasks using an application stored on the computer readable medium.

6. The computer readable medium of claim 5 wherein: the set of instructions are operable to cause the application to be copied to a hard drive of the computer.

7. A computer configured according to instructions stored on a computer readable medium to perform a set of tasks comprising:
 a) receiving, from a user at a remote user computer:
   i) an indication of the user opting in to a time release messaging program;
   ii) a mobile phone number for the user;
   iii) a prescription refill schedule for the user; and
   iv) an identification code for a media device provided to the user, wherein the media device comprises a first video segment featuring a prescribing physician for the user and a plurality of additional video segments featuring physicians other than the prescribing physician, and wherein the media device is operable to configure the remote user computer to:
     request a physician identification code from the user;
     in response to receiving the physician identification code from the user, wherein the physician identification code received from the user is linked to the prescribing physician, play the first video segment for the user; and
     in response to receiving a physician identification code linked to a physician other than the prescribing physician, retrieving a video segment from the plurality of additional video segments, wherein the retrieved video segment from the plurality of additional video segments features the physician other than the prescribing physician linked to the received physician identification code;
 b) sending a new video segment associated with the identification code to the remote user computer;
 c) receiving a signal indicating the location of a mobile device associated with the mobile phone number for the user; and
 d) based on:
   i) physical proximity of the mobile device to a pharmacy;
   ii) temporal proximity of a date when the prescription refill schedule indicates that a prescription should be refilled;
   sending a message to the mobile phone number for the user indicating that the prescription should be refilled.

8. A computer as claimed in claim 7, wherein:
 a) based on the user opting in to the time release messaging program, messages are presented to the user via the remote user computer at intervals starting with opting in to the time release messaging program;
 b) the set of tasks comprises:
   i) based on a query from the remote user computer, sending an update message indicating that an update associated with a message to be presented to the user is available; and
   ii) based on a confirmation signal from the remote user computer indicating that the user has opted into receiving the update, sending the update to the remote user computer, wherein the update comprises a modification to the intervals at which messages are presented to the user via the remote user computer.

9. A computer as claimed in claim 7, wherein the message sent to the mobile phone number indicating the prescription should be refilled comprises data which, when entered by a pharmacist at the pharmacy, automatically provides information necessary to adjudicate a claim for the refill.

10. A non-transitory computer readable medium, having stored thereon a set of instructions operable to configure a computer to perform a set of tasks comprising:
 a) installing, from the non-transitory computer readable medium to a memory of the computer:
   i) a message, the message comprising a content element comprising content specific to a pharmaceutical from a prescription from a prescribing physician;
   ii) a presentation schedule comprising a period;
 b) presenting the message according to the presentation schedule, wherein presenting the message according to the presentation schedule comprises presenting the message:
   i) during a first time period, wherein the first time period starts with an enrollment in a patient assistance program and has a duration equal to the period from the presentation schedule;
   ii) during each of a plurality of subsequent time periods, wherein each of the subsequent time periods starts with a previous presentation of the message, and has a duration equal to the period from the presentation schedule;
 c) making a request for an identification code linked to the prescribing physician;
 d) in response to receiving the identification code, presenting a video segment in which the prescribing physician was recorded;
 wherein:
 A) the video segment in which the prescribing physician was recorded is a video segment from a plurality of video segments stored on the non-transitory computer readable medium;
 B) the plurality of video segments comprises a set of physician video segments featuring physicians other than the prescribing physician;
 C) each physician video segment from the set of video segments corresponds to a physician identification code linked to the physician other than the prescribing physician featured in the other physician video segment; and
 D) the set of tasks the instructions stored on the non-transitory computer readable medium is operable to configure the computer to perform comprises:
   I) in response to receiving a physician identification code linked to a physician other than the prescribing physician featured in a physician video segment, retrieving the physician video segment featuring the physician other than the prescribing physician.

11. The non-transitory computer readable medium of claim 10, wherein the set of tasks the data stored on the non-transitory computer readable medium is operable to configure the computer to perform further comprises:
 a) receiving a dosage schedule;

b) storing the dosage schedule on the memory of the computer;
c) determining a time for providing a medication reminder, wherein the time is determined based on identifying a time which precedes a time when the dosage schedule indicates that the first patient should take the medication; and
d) providing the medication reminder at the determined time.

12. The non-transitory computer readable medium of claim 11, wherein:

a) providing the medication reminder at the determined time comprises displaying the message on a display device of the computer; and
b) the set of data is operable to configure the computer to perform the set of tasks, including providing the medication reminder at the determined time, without requiring a connection to any remote system.

* * * * *